United States Patent [19]

Bethea, III et al.

[11] 4,201,225
[45] May 6, 1980

[54] METHOD AND APPARATUS FOR MEASURING STIMULATED ACOUSTIC REFLEX LATENCY TIME

[76] Inventors: James W. Bethea, III, 1421 Rosedown St., Longview, Tex. 75604; O. Clayton Mitchell, 905 Judson Rd.; George B. Richards, 805 Coleman, both of Longview, Tex. 75601

[21] Appl. No.: 830,162

[22] Filed: Sep. 2, 1977

[51] Int. Cl.$^2$ ............................................... A61B 5/12
[52] U.S. Cl. .................................... 128/746; 179/1 N
[58] Field of Search .................... 128/2 N, 2 Z, 2.1 B, 128/2.1 M, 731–733, 746; 73/585; 179/1 N

[56] References Cited

U.S. PATENT DOCUMENTS

| | | | |
|---|---|---|---|
| 3,334,622 | 8/1967 | Brech | 128/2 V |
| 3,757,769 | 9/1973 | Arguimbau et al. | 73/585 |
| 3,882,848 | 5/1975 | Klar et al. | 73/585 |
| 3,949,735 | 4/1976 | Klar et al. | 73/585 X |
| 4,007,731 | 2/1977 | Griffiths et al. | 179/1 N X |
| 4,009,707 | 3/1977 | Ward | 179/1 N X |
| 4,079,198 | 3/1978 | Bennett | 73/585 X |

OTHER PUBLICATIONS

Hooper, R. E., "Electrocochleography," Surgical Forum, vol. 23, 1972, pp. 475–476.
Krogh, H. J., "The Concept of a Portable & Programmable Tape-Recorder Equipment for use with Electric Response Audiometry," MBEC, vol. 15, pp. 179–183, Mar. 1977.
Guillet, R. et al., "Digital Latencymeter," MBEC, vol. 15, pp. 202–204, Mar. 1977.
Stepanain, H., "Recording in 3D-II," Aust. Elect. Engr., Jan. 1975.
Bird, R., "Computer-Controlled System for Recording Modification & Presentation of Two-Channel Musical Stimuli," Behav. Research Maths & Instr., vol. 8, No. 1, pp. 24–28, Feb. 1976.

*Primary Examiner*—Robert W. Michell
*Assistant Examiner*—Francis J. Jaworski
*Attorney, Agent, or Firm*—Arnold, White & Durkee

[57] ABSTRACT

In a hearing test apparatus, a continuous tone of constant frequency is applied to one ear of a patient. A second tone is initiated in an ear of the patient and the resulting response of the intra-aural muscles is detected by measuring the change in ear canal compliance. A clock circuit measures the time period from the input of the second frequency tone to the point of response of the intra-aural muscles. This reflex latency time provides an objective measurement useful in evaluating a patient's hearing ability.

14 Claims, 5 Drawing Figures

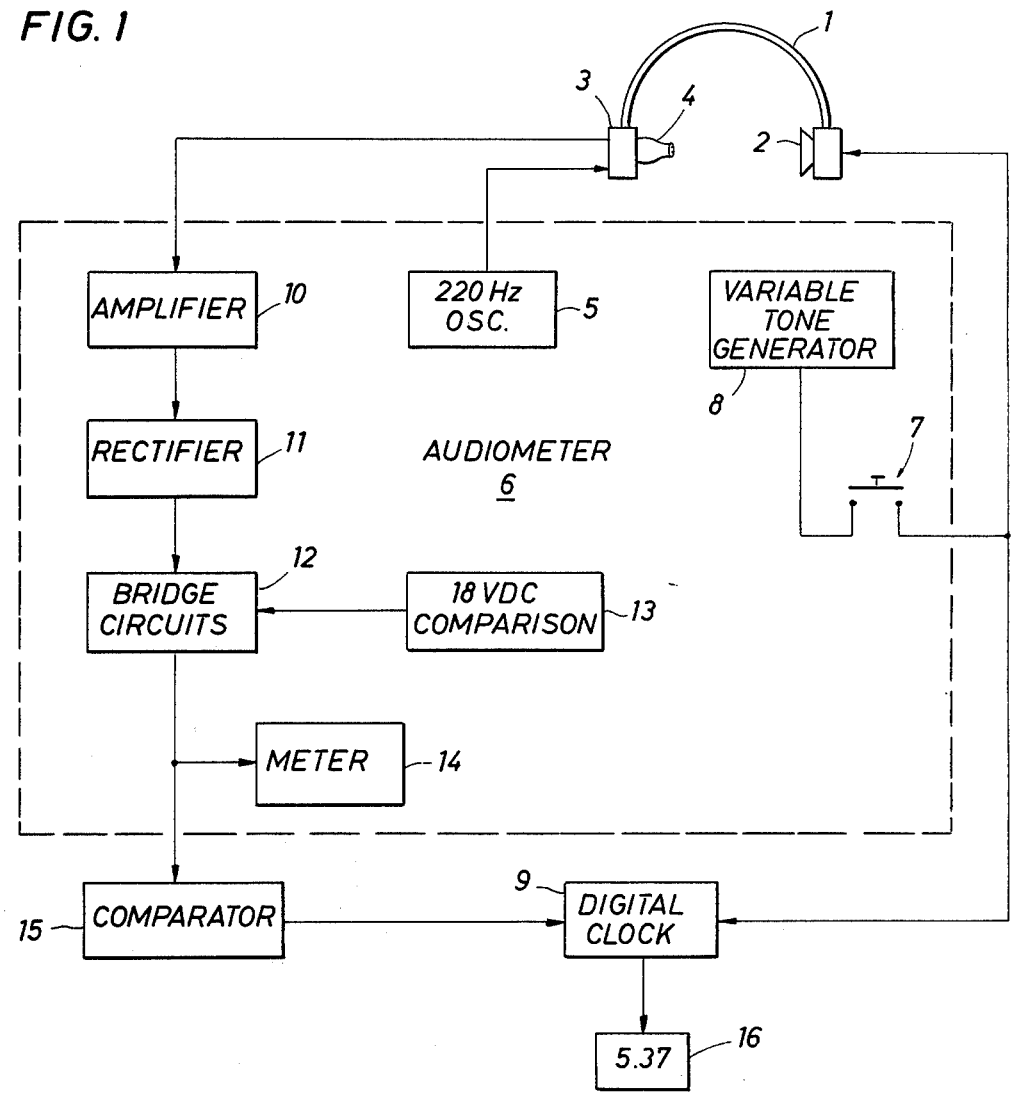
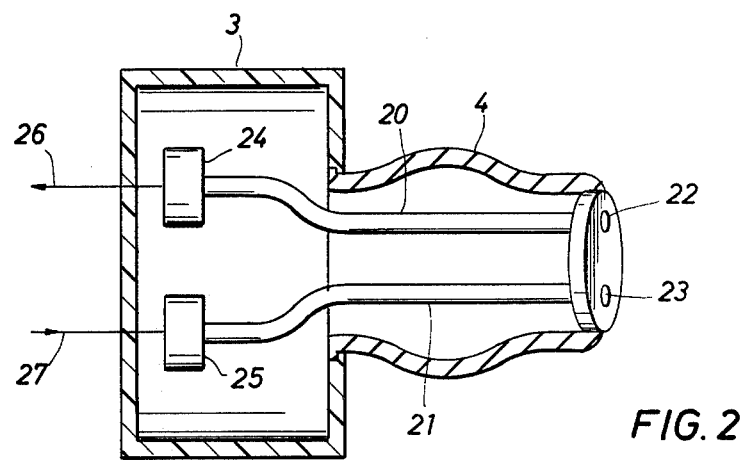

METHOD AND APPARATUS FOR MEASURING STIMULATED ACOUSTIC REFLEX LATENCY TIME

BACKGROUND OF THE INVENTION

1. Field of the Invention

This invention relates generally to a novel audiometric device and more particularly is concerned with the field of acoustic impedance audiometry.

2. Description of the Prior Art

The conventional method of testing hearing has traditionally utilized a machine capable of producing an audio output at a set frequency, with the output variable in frequency and loudness. A skilled operator is required to select the proper sequence of tones, at different frequencies and sound amplitudes, which are transmitted successively to the ear of a test subject who then indicates, as by depressing a push button switch, whether each sound was or was not heard. The test subject's response is subsequently analyzed to compile a profile of hearing ability. This method is disadvantageous because it is time consuming, requiring a number of test "runs" to collect sufficient data. Furthermore, a skilled operator must be provided to properly perform the test. Such a test may produce inaccurate data because the tested subject's response can be highly subjective due to the way in which sounds are perceived. Because the subject of such a test necessarily must actively participate in the test, this method cannot be used to evaluate the hearing of a patient who is unable or unwilling to respond, such as a young child. Although such conventional hearing test methods are normally conducted with the test subject in an acoustically isolated enclosure, high ambient noise levels can interfere with the test subject's perception of the test tones and thereby introduce further error into the test results.

In response to the need for a more accurate and reliable method of testing hearing ability, techniques have been developed which measure an involuntary reaction of the tested subject to an applied sound. The test method thus can be made independent of the subject's conscious perception of the sound stimulus, while providing an indication of hearing proficiency. U.S. Pat. No. 4,007,731, to Griffiths et al., for example, describes a testing method which utilizes an observed cause-and-effect relationship between the applied sound stimulus and a change in heart beat, and U.S. Pat. No. 3,799,146, to John, teaches a technique for analyzing brain wave activity to detect the presence of a neural response to an applied sound.

One of the more useful involuntary physiological indications of a reaction to a sound stimulus is that of the intra-aural muscles which are located in the middle ear. These muscles exhibit a characteristic contraction in response to sound stimuli. Such a contraction will in turn cause a change in the tension of the eardrum. This change in eardrum tension produces a change in equivalent volume in the ear canal. When that ear canal is pressure sealed by an ear plug, this change in volume can be measured, and will produce an electrical signal from a transducer exposed to the sealed ear canal. This electrical signal can then be calibrated to provide a measure of the compliance, or flexibility, of the eardrum. The correlation between the presence of an intra-aural muscle reflex and a test subject's hearing proficiency is known in the art. For example, U.S. Pat. No. 3,395,697, to Mendelson, describes a device which detects the presence or absence of a change in compliance in response to an applied stimulus which can be varied in frequency and amplitude. U.S. Pat. Nos. 3,949,735, to Klar, and 4,009,707, to Ward, disclose refinements of this technique of evaluating hearing ability.

While the significance of the intra-aural muscular contraction for diagnosis of hearing deficiencies is thus known in the art, the use of this phenomena has been limited. Known methods for measuring the reflex are designed to discriminate between the presence or absence of a response of the intra-aural muscles. The prior art techniques, however, have not recognized the clinical significance of the time characteristics of this response. No hearing test method has heretofore utilized as a diagnostic parameter the magnitude of the intra-aural muscle response as a function of the time lapse after an applied sound stimulus.

It is therefore a feature of this invention to provide an improved method and apparatus for testing hearing which measures the involuntary response time of the hearing mechanism.

It is another feature of this invention to provide an improved diagnostic method and apparatus to increase the accuracy of a hearing test.

It is another feature of this invention to provide an improved diagnostic method and apparatus which simplifies the procedure required for a hearing test.

It is another feature of this invention to provide an improved diagnostic hearing test method and apparatus which is less dependent on the subjective response of the patient tested.

It is another feature of this invention to provide an improved method for testing hearing which requires a minimum of time to conduct.

It is another feature of this invention to provide an improved method and apparatus for testing hearing which is less dependent on the skills of a trained operator.

It is another feature of this invention to provide an improved method and apparatus for testing hearing which is less subject to error in the presence of ambient noise levels.

It is another feature of this invention to provide an improved acoustic impedance apparatus for testing hearing which is less expensive to produce.

It is an additional feature of this invention to provide a compliance testing method which does not require an air tight seal in the ear.

SUMMARY OF THE INVENTION

A continuous tone at a constant frequency is applied to one ear of a patient. The middle ear exhibits a constant compliance in response to this continuous tone.

The machine operator chooses a second tone at a desired frequency and sound level, and applies that tone to either the first or second ear of the patient, causing a clock circuit to begin a timing sequence. The motion of the middle ear mechanism in response to the second tone is detected as a change in compliance in the ear canal. Upon the detection of this response, the clock circuit is automatically stopped and the machine thereby provides a quantitative reading of the reflex latency time of response of the intra-aural muscles to an applied sound stimulus.

The test may be conducted so as to measure either the contralateral or ipsilateral reflex latency time. To measure the contralateral response, the second tone is applied in one ear, while the response of the hearing system is detected in the other ear. For an ipsilateral reflex test, both tones are applied to the same ear in which the response is detected.

The timing circuitry of the apparatus may optionally provide either a read-out of the quantitative time of response or a go-no go system of lights, in which case the apparatus would indicate whether or not the test subject's hearing system responded quickly enough to fall within an acceptable time limit.

BRIEF DESCRIPTION OF THE DRAWINGS

So that the manner in which the above-recited features, advantages, and objects of the invention, as well as others which will become apparent, are attained and can be understood in detail, a more particular description of the invention briefly summarized above may be had by reference to the embodiments thereof illustrated in the appended drawings, which form a part of this specification. It is to be noted, however, that the appended drawings illustrate only typical embodiments of the invention and are not to be considered limiting of its scope, for the invention may admit of other equally effective embodiments.

In the drawings:

FIG. 1 schematically depicts, in block diagram form, the circuitry of one preferred embodiment of the present invention, utilizing a contralateral testing method.

FIG. 2 illustrates in greater detail and in partial sectional view the earplug utilized in the embodiment of FIG. 1.

DETAILED DESCRIPTION OF A PREFERRED EMBODIMENT OF THE INVENTION

Figure 3:
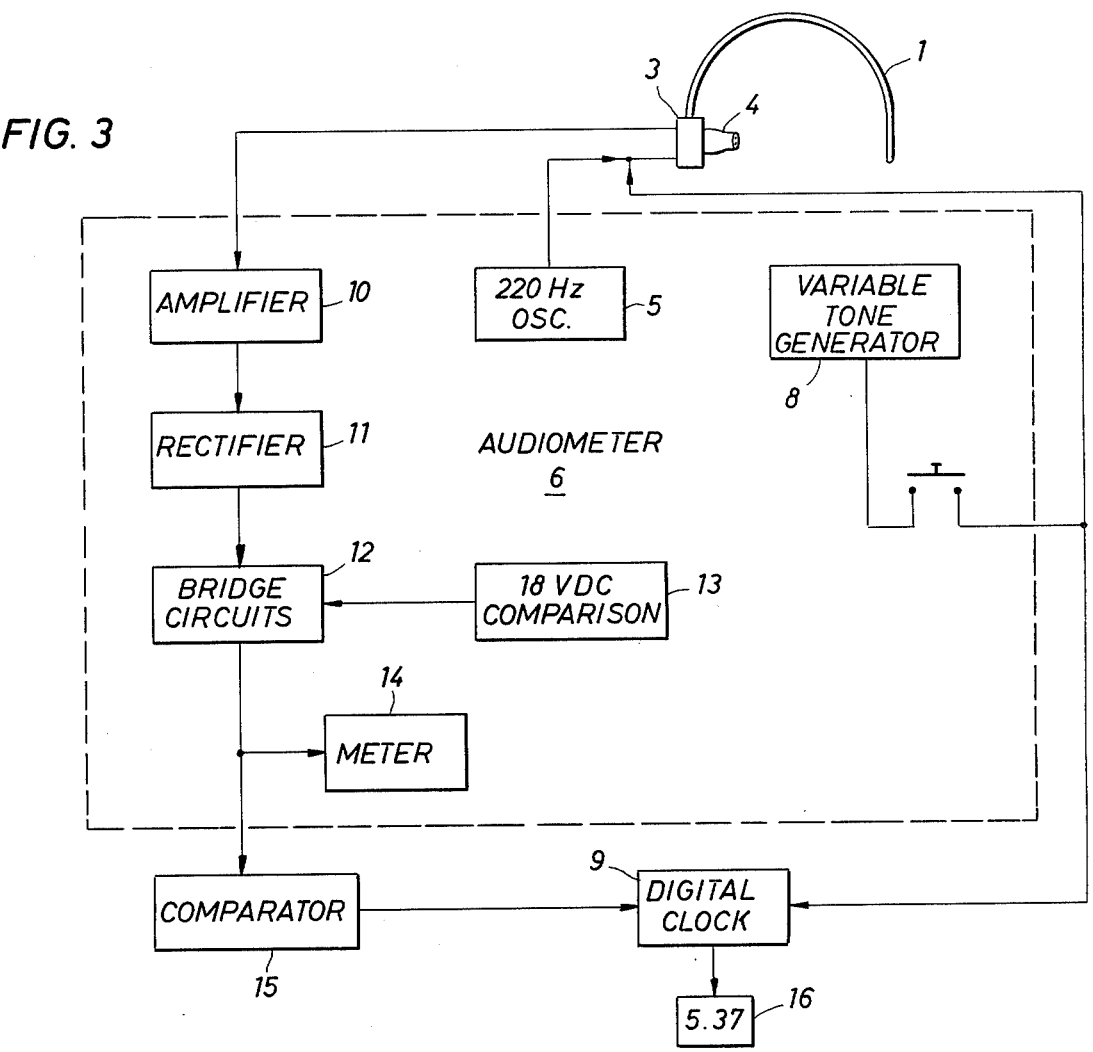
FIG. 3 is a schematic view of an alternative embodiment of the invention, which measures the ipsilateral reflex latency time.

Referring to the drawings, FIG. 1 illustrates one preferred embodiment of the invention, which may best be described by detailing the method in which the apparatus is operated, as follows. The patient whose hearing is to be tested is positioned with headset 1 on his head, with earphone 2 placed over the left ear and with earplug 3 placed into the right ear. The left and right ear designations in this description are arbitrarily made, for purposes of convenience and clarity of the discussion. Those skilled in the art will appreciate that the positions of the earplug and earphone may be reversed with respect to the patient's ears and an identical but symmetrically reversed test sequence will be achieved.

Earphone 2 may be any suitable earphone known by those skilled in the art to be adequate for use in a hearing test apparatus. Earplug 3 is of the pressure-sealing type known in the art, wherein means are provided to pressure seal the ear canal during the test sequence. Included in earplug 3 are input and output microtransducers, as more fully illustrated in FIG. 2 and described below. Earplug 3 is placed into the right ear in such a fashion that the tip 4 of earplug 3 provides a seal for the ear canal which limits the volume parameter of the ear canal to within the measuring capabilities of the test instrumentation. One advantage of the present invention is that an air tight seal is not necessary.

An audiometer 6, consisting of variable tone generator 8, 220 Hz oscillator 5, amplifier 10, rectifier 11, bridge circuit 12, 18 VDC comparison 13, and meter 14 components, is included as an element in the device of the invention, as illustrated in FIG. 1. Audiometer 6 may be any standard audiometer, familiar to those skilled in the art, which is equipped to provide an output which is variable in amplitude and frequency. Typical output ranges which serve adequately in this application are an amplitude varying from 0–125 dB SPL and a frequency selectable between 125–20,000 Hz. One model which has performed adequately in an embodiment of this invention is the DI 75A acoustic impedance audiometer.

To begin the test sequence of the machine, a constant 220 Hz tone from oscillator 5 is applied to the right ear of the patient through a microtransducer contained within earplug 3. It will be appreciated by those skilled in the art that the ear canal will produce a constant level of compliance in responding to this tone of constant frequency and amplitude. To initiate a reflex response test, the operator of the machine applies a tone pulse to the left ear of the patient through earphone 2 by depressing a pushbutton 7 on audiometer 6. Pushbutton 7 connects the output of variable tone generator 8 to earphone 2, thereby causing a tone at the selected frequency and amplitude to be transmitted to the left ear of the test subject. When the operator applies the sound pulse to headphone 2, the circuitry of the apparatus applies the same pulse to the input of digital clock 9 and thereby starts the clock on a timing sequence.

When the sound stimulus is applied to the patient's left ear, the right ear, through the neural hearing mechanism, will exhibit a response to that stimulus. This response, which can be detected by measuring the resulting pressure change in the sealed right ear canal, is in the nature of a reflex response of the intral-aural muscles. The reflex response causes a movement of the eardrum, which in turn causes the resultant pressure change in the ear canal.

Within earplug 3, a second microtransducer detects the change in compliance and transmits a corresponding electrical signal to amplifier 10, where the weak signal is amplified and routed to rectifier 11. The rectified DC signal is then applied to bridge circuit 12 which, using an 18 VDC source 13 as a reference standard, quantifies the magnitude of this signal. The meter 14 provides an indication to the operator of the level of compliance being measured by the instrumentation at any moment. From the bridge circuitry the signal enters a comparator circuit 15, further illustrated in FIG. 5, which, when the compliance changes due to the reflex response, sends a termination signal to the digital clock 9. Digital clock 9 may be any suitable standard model available. One clock which has performed adequately in an embodiment of this invention is the Lafayette model 54419-A clock/counter. Upon receiving a signal from the comparator, the clock stops its timing sequence and provides a digital numerical readout 16 indicating the reflex latency time required for the patient's hearing system to respond to the applied sound stimulus. If the measured time exceeds an empirically determined acceptable value, physical problems with the inner ear or neural malfunctions could be present and further diagnosis is thereby indicated to determine the exact nature of the hearing problem and implement corrective treatment.

FIG. 2 illustrates a detailed view of the earplug 3 of FIG. 1. The earplug is provided with a flexible tip 4, which seals the ear canal against ambient air pressure, and microtransducers 24 and 25. Path 27 indicates a signal input to microtransducer 25 from the 220 Hz oscillator 5, and path 26 indicates a signal output from microtransducer 24 to the amplifier 10 of FIG. 1. Acoustic tubing 20 and 21 provides a connection between microtransducers 24 and 25, respectively, and the ear canal, through openings 22 and 23. Devices suitable for use as the earplug 3 in this apparatus are known to the art. One such device, for example, which includes the design features of the earplug as shown and would perform adequately in this application, is disclosed in U.S. Pat. No. 4,014,320, to Richards.

FIG. 3 illustrates an alternative embodiment in which the device may be used to test the ipsilateral reflex latency response time for the patient's hearing. In this embodiment, the pulse tone is applied, through the earplug, to the same ear to which the control tone of 220 Hz is applied. The remaining circuitry is similar to that described in the embodiment of FIG. 1, but the test as made by the alternative embodiment of FIG. 3 is not dependent on a bilateral response and is of simplified construction, since the test device need be applied to only one ear of the patient.

Figure 4:
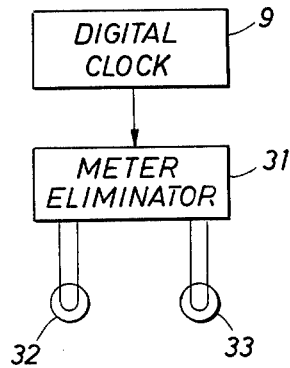
FIG. 4 illustrates an alternative embodiment of the timing circuitry of FIGS. 1 and 3 which provides a go-no go indication of the test results.

FIG. 4 illustrates an alternative embodiment for the timing circuitry of either FIG. 1 or FIG. 3. In this embodiment, a response period analyzer 31 analyzes the response period measured by the digital clock 8 and provides power to either light 32 or light 33, depending upon whether the response period is longer or shorter than a maximum acceptable response time. This embodiment would be particularly useful when the machine is employed by an operator who has not had special training in audiometry. Thus, for example, this embodiment of the device could be used by a school nurse to rapidly screen a large number of school children for possible hearing deficiencies. Whenever a tested child's response time was within the acceptable limit, a green "normal" light, such as light 32, would glow. Should the test indicate a response time which was excessive, a red "problem" light, such as light 33, would indicate a problem and that child could be referred to expert hearing diagnosticians for more extensive diagnosis and testing.

Figure 5:
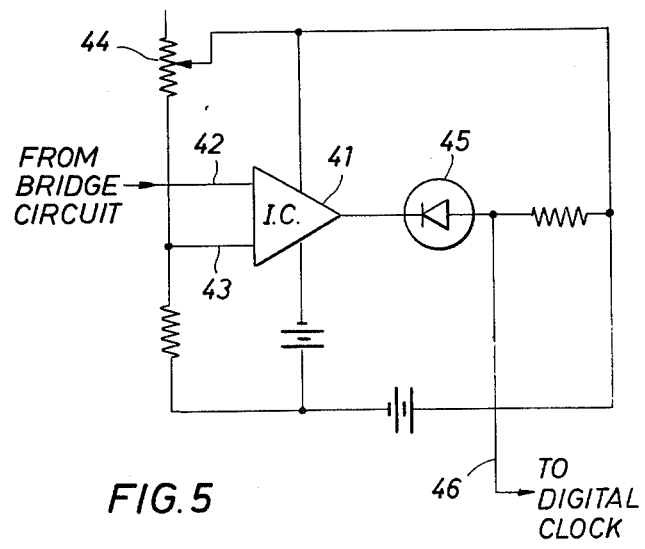
FIG. 5 details in schematic form the comparator circuitry of FIGS. 1 and 3.

FIG. 5 depicts the comparator circuitry in greater detail. Potentiometer 44 is adjusted so that a very small voltage is applied to I.C. 41. When the bridge circuit generates a positive voltage, this voltage is applied to I.C. 41 through lead 42. If the voltage applied through lead 42 equals or exceeds the voltage applied through lead 43, I.C. 41 acts as a gate, allowing a large current to flow through diode 45. This voltage is tapped off through lead 46 and stops the timing sequence of digital clock 9 in FIGS. 1 and 3.

It is apparent that an audiometric testing apparatus and method has been described which substantially encompasses the features, objects, and advantages described herein. Although the invention has been described in conjunction with these specific embodiments, it will be understood that the invention is not limited thereto, since many alternatives, modifications, and variations will be apparent to those skilled in the art. Accordingly, it is intended that all such other forms of the invention fall within the spirit and scope of the method and apparatus as described herein.

What is claimed is:

1. A method for computing the stimulated response time of the human auditory system, comprising:
   maintaining a first tone at a constant frequency and sound pressure level in one ear, of a patient,
   introducing a second tone into the same or the other ear, of said patient,
   detecting the change in acoustic compliance of one of said ears corresponding to the introduction of said second tone, and
   calculating the time delay between the introduction of said second tone and said change in acoustic compliance, and comparing said time to an acceptable time delay value as a measure of the hearing ability of the patient.

2. The method of claim 1 in which:
   said first tone is applied to a first ear,
   said second tone is applied to a second ear, and
   the detection of said change in acoustic compliance is accomplished in said first ear, thereby providing a measure of the stimulated contra-lateral acoustic reflex latency time.

3. The method of claim 1 in which:
   said first tone is applied to a first ear,
   said second tone is applied to said first ear, and
   the detection of said change in acoustic compliance is accomplished in said first ear, thereby measuring the stimulated ipsilateral acoustic reflex latency time.

4. A method for measuring the reflex latency time of the intra-aural muscles, which comprises:
   applying to one ear of a patient a continuous first tone,
   applying by operator action a second tone to the same or the other ear of said patient,
   initiating a time period upon the activation of said second tone,
   detecting a change in the acoustic compliance of one of said ears to said second tone and generating a signal according to that change, and
   utilizing said signal to stop said time period, thereby measuring reflex latency time.

5. The method of claim 4 in which said first tone comprises a continuous tone of approximately 220 Hz.

6. The method of claim 4 in which said second tone comprises a tone of a fixed frequency between approximately 125 Hz and approximately 20,000 Hz.

7. The method of claim 4 in which said second tone is applied at varying levels of loudness.

8. The method of claim 4 in which said second tone is variable in frequency.

9. An instrument for measuring the reflex latency time of the intra-aural muscles, comprising:
   a constant-tone sound generator adapted to apply a continuous first tone to an ear of a patient,
   a second sound generator adapted to apply an operator-activated second tone to the same or the other ear of the patient,
   electronic circuit means for detecting a change in the acoustic compliance of one of said ears to said second tone and generating a signal corresponding to that change, and,
   timing means coupled to said second sound generator and to said circuit detecting means, said timing means being initiated by said second sound generator and terminated responsive to said detection circuit means upon detection of said acoustic compliance change, whereby said timing means produces an output representative of acoustic reflex latency time.

10. The instrument of claim 9 wherein said constant-tone sound generator comprises an oscillator generating an output of approximately 220 Hz.

11. The instrument of claim 9 wherein the second sound generator comprises an audiometer with an output of variable frequency and intensity.

12. The instrument of claim 9 wherein the timing means comprises a high frequency clock circuit.

13. The instrument of claim 9 wherein said timing means provides a digital read-out of the reflex latency time.

14. The instrument of claim 9 wherein said timing means includes a read-out system of lights, providing a threshold indication of hearing problems.

* * * * *